(12) United States Patent
Yamazaki

(10) Patent No.: US 7,361,157 B2
(45) Date of Patent: Apr. 22, 2008

(54) SYRINGE-PUMP DRIVING APPARATUS

(75) Inventor: Masao Yamazaki, Hachioji (JP)

(73) Assignee: Jasco Corporation, Hachioji-shi, Tokyo (JP)

( * ) Notice: Subject to any disclaimer, the term of this patent is extended or adjusted under 35 U.S.C. 154(b) by 155 days.

(21) Appl. No.: 11/219,373

(22) Filed: Sep. 2, 2005

(65) Prior Publication Data

US 2006/0118199 A1 Jun. 8, 2006

(30) Foreign Application Priority Data

Sep. 6, 2004 (JP) ............................. 2004-258215

(51) Int. Cl.
*A61M 37/00* (2006.01)
(52) U.S. Cl. .................................... 604/131
(58) Field of Classification Search ........ 128/DIG. 12, 128/DIG. 13; 604/131, 154, 65, 66, 67, 604/132–139, 156–157
See application file for complete search history.

(56) References Cited

U.S. PATENT DOCUMENTS 4,087,248 A * 5/1978 Miles ......................... 436/506
5,047,012 A * 9/1991 Leuschner et al. ............ 604/32
5,988,236 A 11/1999 Fawcett
6,387,077 B1 * 5/2002 Klibanov et al. ........... 604/181
6,869,571 B2 * 3/2005 Ingenhoven et al. ........ 422/100

\* cited by examiner

*Primary Examiner*—Manuel Mendez
(74) *Attorney, Agent, or Firm*—Rankin, Hill & Clark LLP

(57) ABSTRACT

It is an object of the present invention to provide a multiple-syringe-pump driving apparatus having superior liquid discharging and drawing-up precision. A syringe-pump driving apparatus of the present invention is used for controlling discharge from and drawing-up into a plurality of syringe pumps interconnected in parallel. The syringe-pump driving apparatus 10 comprises: a syringe holder 18 for supporting syringes 14a to 14h of the plurality of syringe pumps 12a to 12h so as to be arranged in parallel; a plunger holder 20 for supporting plungers 16a to 16h contained in the syringes 14a-14h so as to be arranged in parallel; three or more drive screws 24-1 to 24-3 for moving the plunger holder 20 and the syringe holder 18 relative to each other in a straight line in a syringe axial direction 30; and one or a plurality of motors 26 serving as a source of motive power for the drive screws 24-1 to 24-3. The three or more drive screws 24-1 to 24-3 are connected to the syringe holder 18 or the plunger holder 20 at three or more driving points to transmit motive power to the syringe holder 18 or the plunger holder 20 via the three or more driving points.

4 Claims, 5 Drawing Sheets

10:SYRINGE-PUMP DRIVING APPARATUS

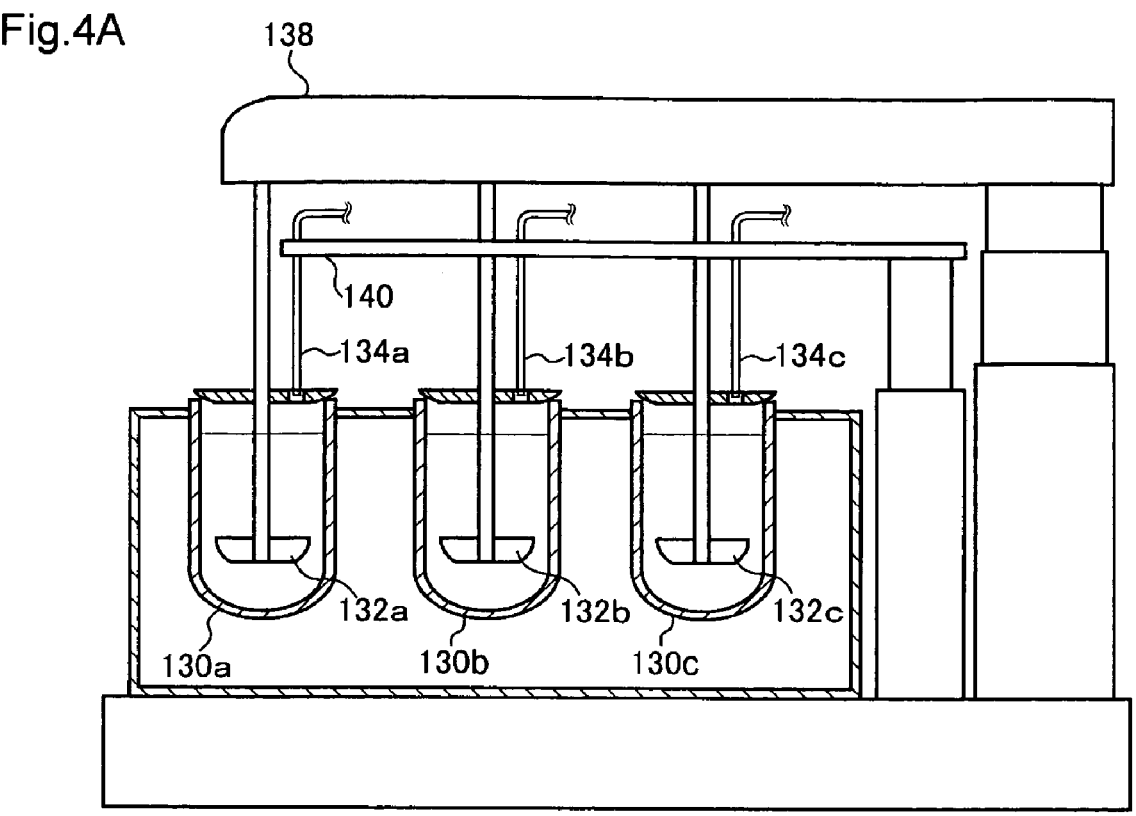

SYRINGE-PUMP DRIVING APPARATUS

RELATED APPLICATIONS

This application claims priority to the Japanese Patent Application 2004-258215 dated on Sep. 6, 2004 and is hereby incorporated with reference for all purposes.

BACKGROUND OF THE INVENTION

1. Field of the Invention

The present invention relates to an improved driving mechanism for a syringe-pump driving apparatus for controlling the discharge and drawing-up of a plurality of syringe pumps.

2. Description of the Related Art

Syringe pumps are widely used in a variety of tests and measurements for controlling the amount of liquid discharged and drawn-up with high precision. The amount of liquid discharged and drawn-up is determined by the amount of movement of a plunger, and drive screws are generally used as the driving mechanism therefor.

Driving apparatuses that discharge and draw up liquid in multiple flow paths, by connecting a plurality of syringe pumps in parallel and driving them simultaneously, are also used. One example of such an apparatus is described in U.S. Pat. No. 5,988,236. The syringe-pump driving apparatus described in U.S. Pat. No. 5,988,236 adopts a structure in which a holder that fixes a plurality of syringes is driven by means of a single drive screw, and the holder is kept in balance by means of a plurality of guide rails while moving. However, since the apparatus described in U.S. Pat. No. 5,988,236 has only a single driving point, when the resistance of each syringe is changed due to deterioration, thus degrading the dynamic balance of the holder, it is difficult to move the holder while keeping it straight. As a result, there is a drawback in that the precision of the syringes when discharging and drawing-up liquid is reduced.

SUMMARY OF THE INVENTION

The present invention has been conceived in light of the problems described above, and it is an object thereof to provide a multiple-syringe-pump driving apparatus having superior liquid discharging and drawing-up precision.

A syringe-pump driving apparatus of the present invention is used for controlling discharge from and drawing-up into a plurality of syringe pumps interconnected in parallel. The syringe-pump driving apparatus according to the present invention comprises: a syringe holder for supporting syringes of the plurality of syringe pumps so as to be arranged in parallel; a plunger holder for supporting plungers contained in the syringes so as to be arranged in parallel; three or more drive screws for moving the plunger holder and the syringe holder relative to each other in a straight line in a syringe axial direction; and one or a plurality of motors serving as a source of motive power for the drive screws. The three or more drive screws are connected to the syringe holder or the plunger holder at three or more driving points to transmit motive power to the syringe holder or the plunger holder via the three or more driving points.

In the syringe-pump driving apparatus of the present invention, it is preferable that the positions of the three or more driving points of the drive screws for the syringe holder or the plunger holder are disposed such that the loads acting at the three or more driving points from the syringes and/or the plungers are made substantially equal.

In the syringe-pump driving apparatus of the present invention, it is preferable that the number of the drive screws is three.

In the syringe-pump driving apparatus of the present invention, it is preferable that the apparatus further comprises a fixed support base for fixing one of the syringe holder and the plunger holder, the other holder being moveable.

Since a syringe-pump driving apparatus of the present invention has a structure in which a plunger holder or a syringe holder is moved via three or more driving points, the amount of liquid discharged and drawn-up can be controlled with high precision.

BRIEF DESCRIPTION OF THE DRAWINGS

FIG. 4A and FIG. 4B depict the operation of the dissolution test apparatus shown in FIG. 3.

DESCRIPTION OF THE PREFERRED EMBODIMENT

A preferred embodiment of the present invention will be described below with reference to the drawings.

Figure 1:
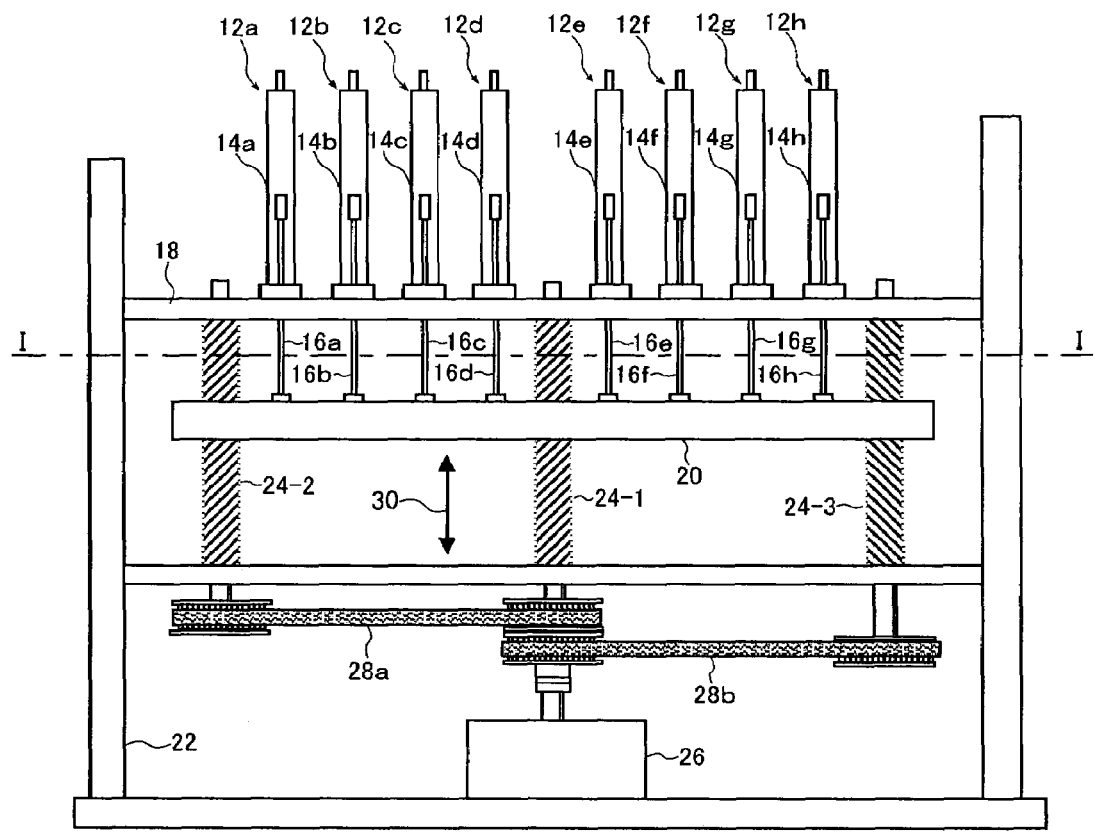
FIG. 1 is an outlined structural view of a syringe-pump driving apparatus according to an embodiment of the present invention.

FIG. 1 is an outlined structural view of a syringe-pump driving apparatus according to an embodiment of the present invention. A syringe-pump driving apparatus 10 shown in FIG. 1 includes a syringe holder 18 for supporting syringes 14a to 14h of a plurality of syringe pumps 12a to 12h so as to be arranged in parallel; and a plunger holder 20 for supporting plungers 16a to 16h corresponding to the syringes 14a to 14h, so as to be arranged in parallel. In this embodiment, eight syringe pumps are illustrated, but the number of syringe pumps is not particularly limited to this number.

The syringe holder 18 and the plunger holder 20 are arranged so as to move in a straight line relative to each other in the axial direction 30 of the syringe pumps 12a to 12h. In this embodiment, the syringe holder 18 is defined as a fixed holder and the plunger holder is defined as a moving holder. More precisely, the syringe holder 18 is fixed to a fixed support base 22, and the plunger holder 20 is configured to be movable with respect to the syringe holder 18.

One end of each of three drive screws 24-1 to 24-3 is supported at the syringe holder 18 and the other end thereof is supported at the fixed support base 22 so as to be rotatable about the axes thereof. The type of drive screws is not particularly limited; for example, ball screws may be preferably used. The plunger holder 20 contacts the drive screws 24-1 to 24-3 at three driving points. The rotary force of the three drive screws 24-1 to 24-3 is converted to a linear driving force for the plunger holder 20 at these driving points. More precisely, three screw followers 25-1 to 25-3 are fixed to the plunger holder 20, and the screw followers 25-1 to 25-3 are engaged with the respective drive screws 24-1 to 24-3 (see FIG. 2). Then, by rotating the drive screws 24-1 to 24-3, the rotary force thereof is converted to linear motion by means of the screw followers 25-1 to 25-3, which is transmitted to the plunger holder 20. In addition, the drive screws 24-1 to 24-3 are connected via belts 28a and 28b to a motor 26 serving as a source of motive power.

Figure 2:
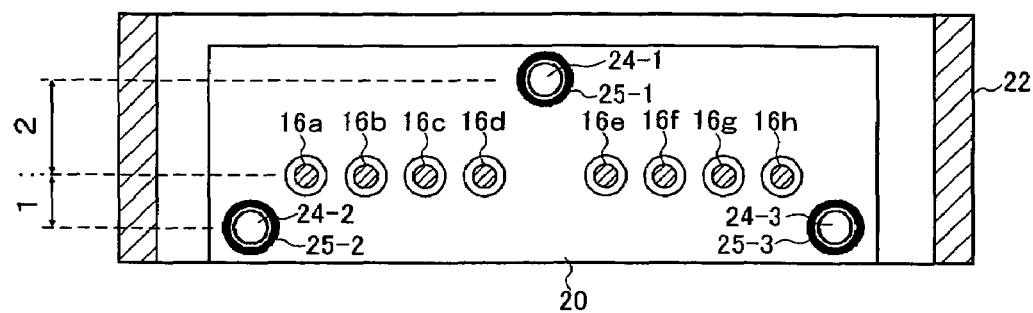
FIG. 2 is a diagram of the syringe-pump driving apparatus according to the embodiment of the present invention, as viewed from a syringe axial direction.

FIG. 2 is a cross-section, taken along I-I in FIG. 1, viewed from the syringe axial direction of the syringe-pump driving apparatus of the present embodiment shown in FIG. 1. As shown in FIG. 2, the positions of the three driving points (the screw followers 25-1 to 25-3) of the three drive screws 24-1 to 24-3 on the plunger holder 20 are preferably disposed such that the loads acting at the three driving points are substantially the same. In the example shown in FIG. 2, two driving points are arranged so as to sandwich the plungers 16a to 16h, which are arranged in parallel in a row, from positions close to both longitudinal sides and the other driving point is positioned close to the center of the row of syringes but shifted transversely. Thus, the three driving points are disposed so as to form an isosceles triangle in which the straight line joining the first two driving points defines a base and the remaining point defines the apex thereof. Moreover, the syringes are disposed on a straight line that passes through a point dividing a perpendicular drawn from the apex to the base in a ratio of 2-to-1 and that is at right angles to the perpendicular.

The above is an outline of the structure of the present embodiment; next, the operation thereof will be described with reference to FIG. 1 again.

The rotary force of the motor 26 is transmitted to the drive screw 24-1 and via the belts 28a and 28b to the drive screws 24-2 and 24-3. Thus, the rotations of the drive screws 24-1 to 24-3 are interconnected with one other.

As described above, driving points for the drive screws 24-1 to 24-3 are defined at three appropriate points on the plunger holder 20, and the rotary forces of the drive screws 24-1 to 24-3 are converted to driving forces in the syringe axial direction 30 of the plunger holder 20 at these driving points. That is, the amount of motion of the moving holder 20 is controlled by controlling the amount of rotation of the drive screws 24-1 to 24-3.

Also, the amount of rotation and the rotation direction of the motor 26 are controlled by a control apparatus, which is not shown, and the amount of motion and the moving direction of the plunger holder 20 are controlled thereby.

As described in U.S. Pat. No. 5,988,236, in a system combining one drive screw and a plurality of guide rails, it is necessary to align the driving point of the drive screw with the center of the load; however, if the load balance is lost because of individual syringe differences occurring due to deterioration of the syringes or the like, smooth motion becomes impossible.

Conversely, since the syringe-pump driving apparatus of the present embodiment has a structure in which it actively moves at three appropriate points on the holder by means of the three drive screws, even if the sliding resistance of the plurality of syringes attached to the holder changes due to deterioration or the like, causing the dynamic balance of the holder to shift, it is possible to achieve precise motion while keeping the holder straight. As a result, the amount of fluid discharged from and drawn up into each syringe is precisely ensured.

With the embodiment described above, the syringe holder is defined as fixed and the plunger holder is defined as moving; conversely, however, the plunger holder may of course be defined fixed and the syringe holder defined as moving.

In the embodiment described above, driving of the three drive screws is performed with a single motor; however, a structure in which a plurality of motors are synchronized to perform driving of the drive screws is also permissible.

In the embodiment described above, the number of the drive screws is three. But the number of drive screws may be above three.

Next, an example in which the syringe-pump driving apparatus of the embodiment described above is used as a liquid discharge mechanism in a dissolution test apparatus will be described. A dissolution test apparatus is used to measure the amount of elution and so on when a tablet-type drug is immersed in a predetermined test solution.

Figure 3:
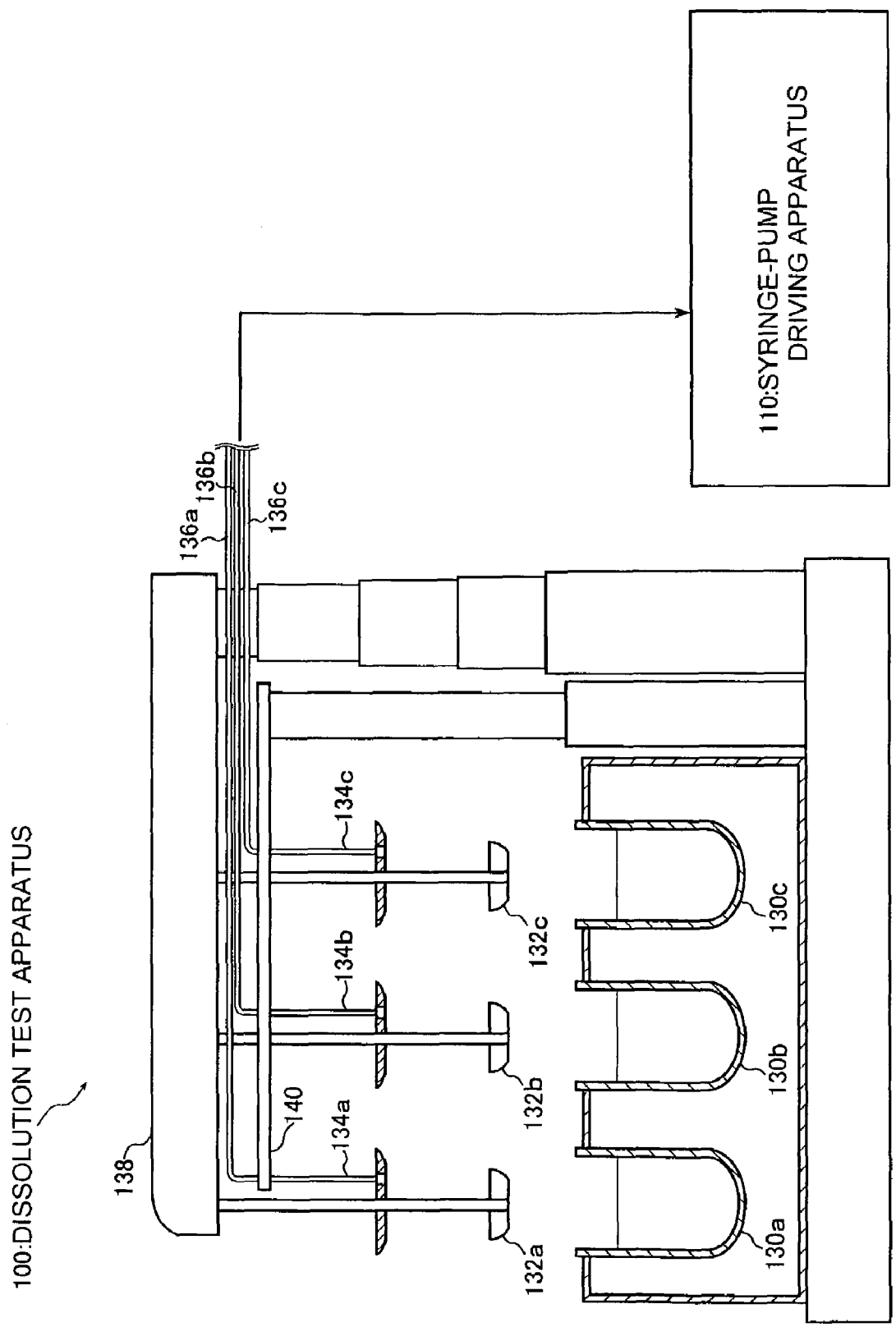
FIG. 3 is an outlined structural view of a dissolution test apparatus provided with the syringe-pump driving apparatus of this embodiment.

FIG. 3 is an outlined structural view of the dissolution test apparatus, partially taken in cross section. A dissolution test apparatus 100 in FIG. 3 includes a plurality of vessels 130a to 130c in which a test solution and a sample are placed; a plurality of mixing paddles 132a to 132c for agitating the liquids in the corresponding vessels 130a to 130c; a plurality of nozzles 134a to 134c for injecting liquids into the vessels 130a to 130c and for drawing up liquids therefrom; a syringe-pump driving apparatus 110; and tubes 136a to 136c for connecting syringes in the syringe-pump driving apparatus 110 with the corresponding nozzles 134a to 134c. The number of vessels, mixing paddles, nozzles, and tubes shown in the figure is three, but it is not particularly limited to this number.

The mixing paddles 132a to 132c are set in an agitator head 138, and the agitator head 138 is configured to be movable upward and downward.

The nozzles 134a to 134c are set in a nozzle head 140, and the nozzle head 140 is also configured to be movable upward and downward. In addition, the agitator head 138 and the nozzle head 140 are configured as independent motion mechanisms.

Figure 4B:
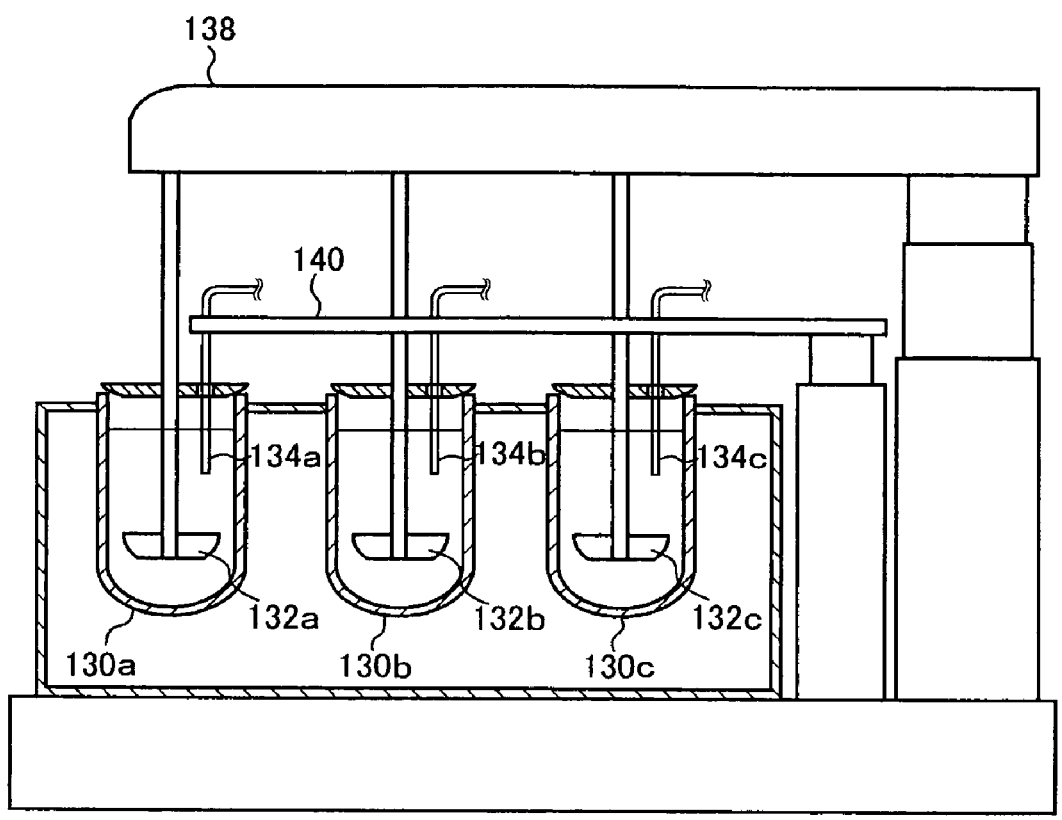

The mixing paddles 132a to 132c and the nozzles 134a to 134c of the dissolution test apparatus 100 stand-by in a raised, preparatory state, as shown in FIG. 3. Then, as shown in FIG. 4A, in order to agitate the contents of the vessels 130a to 130c with the mixing paddles 132a to 132c, first, only the agitator head 138 is moved downward to position the mixing paddles 132a to 132c at predetermined locations inside the vessels 130a to 130c.

After a predetermined time has elapsed, in order to draw up the liquid from inside the vessels 130a to 130c, the nozzle head 140 is also moved downward to position the nozzles 134a to 134c at predetermined locations inside the vessels 130a to 130c. Then, the liquids inside the vessels 130a to 130c are drawn up into the corresponding syringes by the syringe-pump driving apparatus 110.

Thus, the syringe-pump driving apparatus of this embodiment is suitable for use in an apparatus in which it is necessary to precisely discharge and draw up liquid, such as the dissolution test apparatus described above.

What is claimed is:

1. A syringe-pump driving apparatus for controlling discharge from and drawing-up into a plurality of syringe pumps interconnected in parallel, comprising:
   a syringe holder for supporting syringes of the plurality of syringe pumps so as to be arranged in parallel;
   a plunger holder for supporting plungers contained in the syringes so as to be arranged in parallel;
   three or more drive screws for moving the plunger holder and the syringe holder relative to each other in a straight line in a syringe axial direction;
   one or a plurality of motors serving as a source of motive power for the drive screws; and,
   one or more drive belts;

wherein the three or more drive screws are connected to the syringe holder or the plunger holder at three or more driving points to transmit motive power to the syringe holder or the plunger holder via the three or more driving points; and, the rotary force of the motor is directly transmitted to one of the drive screws via the belts to other drive screws, so as the rotations of the drive screws are interconnected with one another.

2. A syringe-pump driving apparatus according to claim 1, wherein the positions of the three or more driving points of the drive screws for the syringe holder or the plunger holder are disposed such that the loads acting at the three or more driving points from the syringes and/or the plungers are made substantially equal.

3. A syringe-pump driving apparatus according to claim 1, wherein the number of the drive screws is three.

4. A syringe-pump driving apparatus according to claim 1, further comprising a fixed support base for fixing one of the syringe holder and the plunger holder, the other holder being moveable.

* * * * *